(12) United States Patent
Iijima et al.

(10) Patent No.: US 8,915,857 B2
(45) Date of Patent: Dec. 23, 2014

(54) METHOD FOR MANUFACTURING OPTICAL DEVICE, OPTICAL DEVICE, AND BIOLOGICAL INFORMATION DETECTOR

(75) Inventors: Yoshitaka Iijima, Nagano (JP); Hideo Miyasaka, Nagano (JP); Satoshi Nakajima, Okaya (JP)

(73) Assignee: Seiko Epson Corporation, Tokyo (JP)

( * ) Notice: Subject to any disclaimer, the term of this patent is extended or adjusted under 35 U.S.C. 154(b) by 410 days.

(21) Appl. No.: 13/022,177

(22) Filed: Feb. 7, 2011

(65) Prior Publication Data

US 2011/0199613 A1  Aug. 18, 2011

(30) Foreign Application Priority Data

Feb. 18, 2010  (JP) .................................. 2010-033058

(51) Int. Cl.
| | |
|---|---|
| *A61B 5/02* | (2006.01) |
| *A61B 5/024* | (2006.01) |
| *A61B 5/00* | (2006.01) |
| *H01L 23/00* | (2006.01) |
| *A61B 5/1455* | (2006.01) |

(52) U.S. Cl.
CPC ............. *A61B 5/02438* (2013.01); *H01L 24/48* (2013.01); *H01L 24/32* (2013.01); *H01L 2224/73265* (2013.01); *H01L 2224/85186* (2013.01); *H01L 2224/48227* (2013.01); *H01L 24/78* (2013.01); *H01L 2224/48091* (2013.01); *H01L 2924/12041* (2013.01); *A61B 5/681* (2013.01); *A61B 5/1455* (2013.01); *H01L 2224/78301* (2013.01); *H01L 2224/32225* (2013.01)
USPC ....................................................... 600/500

(58) Field of Classification Search
USPC ......... 600/301, 500, 310, 319, 323, 347, 473, 600/476, 502, 503
See application file for complete search history.

(56) References Cited

U.S. PATENT DOCUMENTS

| 6,041,247 A * | 3/2000 | Weckstrom et al. .......... 600/323 |
| 2002/0173076 A1 | 11/2002 | Michii et al. |
| 2006/0232288 A1 | 10/2006 | Okane et al. |

(Continued)

FOREIGN PATENT DOCUMENTS

| JP | 08-181165 A | 7/1996 |
| JP | 2000-116611 A | 4/2000 |

(Continued)

OTHER PUBLICATIONS

Extended European Search Report dated May 27, 2011 for the corresponding European Application No. 11154639.6.

*Primary Examiner* — Jacqueline Cheng
*Assistant Examiner* — Puya Agahi
(74) *Attorney, Agent, or Firm* — Global IP Counselors, LLP

(57) ABSTRACT

An optical device comprises a substrate having a first surface and a second surface being opposite the first surface; a light-emitting element having a first center, installed on the second surface; and a light-receiving element having a second center, installed on the first surface. At least a part of the light-emitting element is arranged at a position, overlapping the light-receiving element with respect to a plan view; the light-receiving element, installed after the light-emitting element, has a bonding pad, provided at a position displaced relative to the second center towards a first direction with respect to the plan view; and the first center is provided at a position displaced relative to the second center towards a second direction, being opposite the first direction DR1, with respect to the plan view.

5 Claims, 14 Drawing Sheets

(56) References Cited

U.S. PATENT DOCUMENTS

| | | | |
|---|---|---|---|
| 2006/0241358 A1* | 10/2006 | Al-Ali et al. | 600/301 |
| 2007/0189676 A1 | 8/2007 | Nagasaka | |
| 2008/0097172 A1* | 4/2008 | Sawada et al. | 600/310 |
| 2008/0097221 A1 | 4/2008 | Florian | |
| 2008/0277679 A1* | 11/2008 | Akimoto | 257/94 |
| 2009/0273001 A1* | 11/2009 | Shum et al. | 257/99 |
| 2009/0283779 A1* | 11/2009 | Negley et al. | 257/88 |
| 2010/0056887 A1* | 3/2010 | Kimura et al. | 600/324 |
| 2011/0166462 A1* | 7/2011 | Iijima et al. | 600/500 |

FOREIGN PATENT DOCUMENTS

| | | | | |
|---|---|---|---|---|
| JP | 2003-008052 A | | 1/2003 | |
| JP | 2003-209133 A | | 7/2003 | |
| JP | 2004337605 | * | 2/2004 | A61B 5/145 |
| JP | 2004-337605 A | | 12/2004 | |
| JP | 2009-106376 A | | 5/2009 | |

* cited by examiner

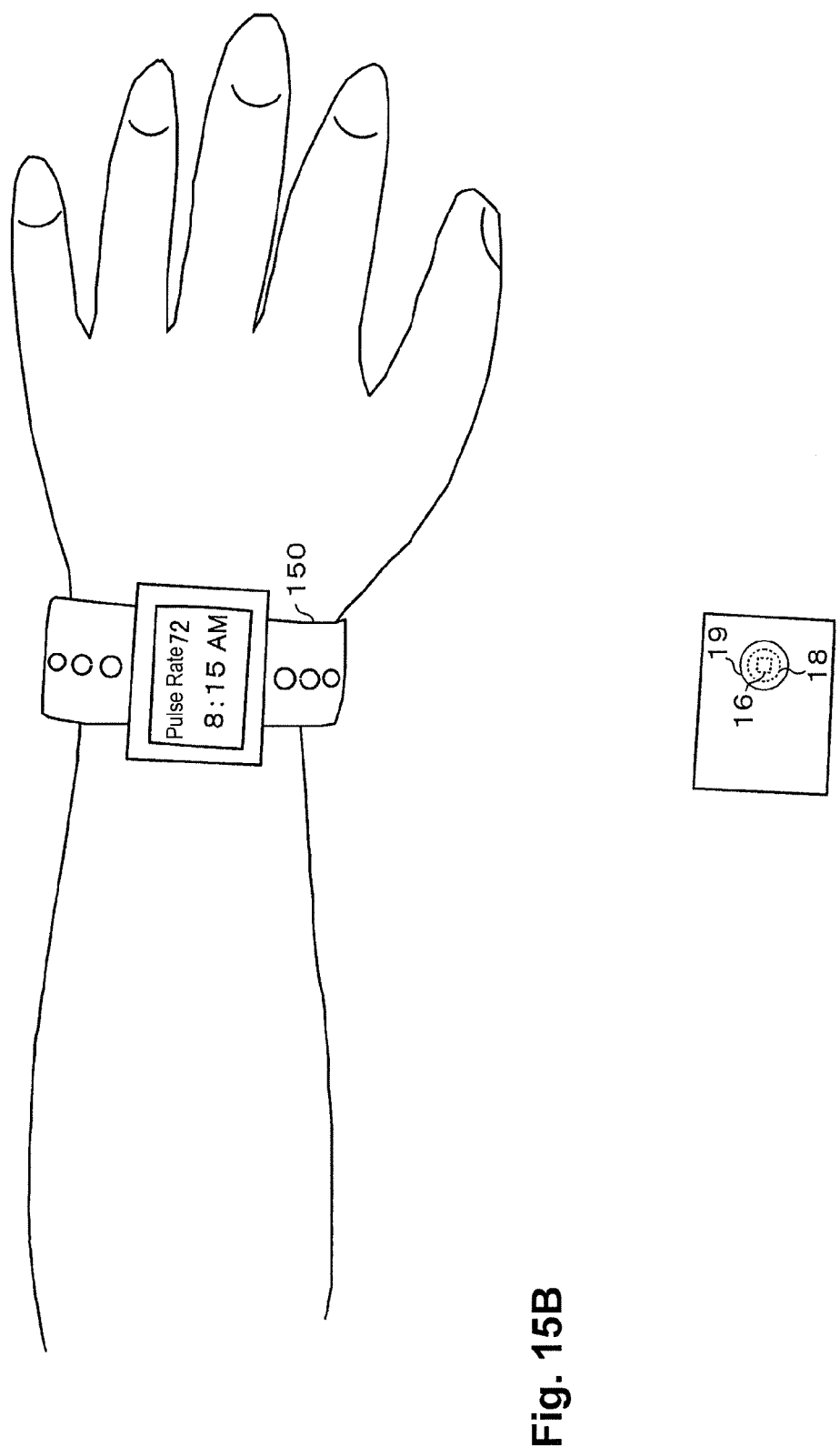

METHOD FOR MANUFACTURING OPTICAL DEVICE, OPTICAL DEVICE, AND BIOLOGICAL INFORMATION DETECTOR

CROSS-REFERENCE TO RELATED APPLICATIONS

This application claims priority to Japanese Patent Application No. 2010-033058 filed on Feb. 18, 2010. The entire disclosure of Japanese Patent Application No. 2010-033058 is hereby incorporated herein by reference.

BACKGROUND

1. Technical Field

The present invention relates to a method for manufacturing an optical device, an optical device, a biological information detector, and the like.

2. Background Technology

A biological information measuring device measures human biological information such as, for example, pulse rate, blood oxygen saturation level, body temperature, or heart rate, and an example of a biological information measuring device is a pulse rate monitor for measuring the pulse rate. Also, a biological information measuring device such as a pulse rate monitor may be installed in a clock, a mobile phone, a pager, a PC, or another electrical device, or may be combined with the electrical device. The biological information measuring device has a biological information detector for detecting biological information, and the biological information detector includes a light-emitting element for emitting light towards a detection site of a test subject (i.e., a user), and a light-receiving element for receiving light having biological information from the detection site. Thus, a biological information detector or the biological information measuring device may have an optical device and be capable of detecting or measuring biological information. A common detector or a measuring device (or in a broader sense, an electronic device) other than a biological information detector or a biological.

In Patent Citation 1, there is disclosed a pulse rate monitor (or in a broader sense, a biological information measuring device). A light-receiving element (e.g., a light-receiving element 12 in FIG. 16 of Patent Citation 1) of the pulse rate monitor receives light reflected at a detection site (e.g., dotted line in FIG. 16 of Patent Citation 1) via a diffusion reflection plane (e.g., reflecting part 131 in FIG. 16 of Patent Citation 1). In an optical probe 1 in Patent Citation 1 (or in a broader sense, a biological information detector), a light-emitting element 11 and the light-receiving element 12 overlap in plan view, and the size of the optical probe is reduced.

JP-A 2004-337605 (Patent Citation 1) is an example of the related art.

SUMMARY

Problems to be Solved by the Invention

FIG. 4 in Patent Citation 1 shows an electrode (or in a narrower sense, a bonding pad) and a wiring (or in a narrower sense, a bonding wire) for the light-receiving element 12. In an instance in which the light-emitting element 11 and the light-receiving element 12 overlap each other with respect to a plan view, a first light-emitting element 111 of the light-emitting element 11 is positioned directly below the bonding pad, as shown in FIG. 5 of Patent Citation 1. According to a configuration described above, when the bonding wire is attached to the bonding pad, it is difficult for the attaching to be made more reliable. Also, the light-emitting element 111 may be damaged during a manufacturing process of such description.

According to several modes of the invention, it is possible to provide a method for manufacturing an optical device, an optical device, and a biological information detector in which the attaching can be performed more reliably when a bonding wire is attached to a bonding pad.

Means Used to Solve the Above-Mentioned Problems

A first aspect of the invention relates to a method for manufacturing an optical device, characterized in comprising:

readying a substrate having a first surface and a second surface that is opposite the first surface;

installing on the second surface a light-emitting element having a first center; installing a light-receiving element having a second center and a bonding pad so that (a) the light-receiving element overlaps with at least a part of the light-emitting element with respect to a plan view;

(b) the bonding pad is displaced relative to the second center towards a first direction with respect to the plan view; and (c) the first center is displaced relative to the second center towards a second direction, which is opposite the first direction, with respect to the plan view; and attaching a bonding wire to the bonding pad while supporting a position directly below the bonding pad.

According to the first aspect of the invention, the bonding pad of the light-receiving element is displaced relative to a center of the light-receiving element (i.e., the second center) towards the first direction with respect to the plan view, and a center of the light-emitting element (i.e., the first center) is displaced relative to the center of the light-receiving element (i.e., the second center) towards the second direction with respect to the plan view. Therefore, the position directly below the bonding pad of the light-receiving element can be supported using a jig or a similar tool. Since a position directly below the bonding pad of the light-receiving element is supported, the bonding pad of the light-receiving element can be immobilized even when the bonding pad is restrained with a bonding tool. The bonding wire can thereby be reliably attached to the bonding pad. As a result, when the bonding wire is attached to the bonding pad, the attaching can be performed more reliably. In an instance in which a space is created in the position directly below the bonding pad of the light-receiving element, it is possible to avoid installing the light-emitting element in the position directly below the bonding pad of the light-receiving element. Therefore, it is possible to prevent the light-emitting element from being damaged when the bonding wire is attached to the bonding pad.

According to a second aspect of the invention, the light-emitting element may be installed on the second surface with a first reflecting part interposed between, the first reflecting part adapted for reflecting light emitted by the light-emitting element and the bonding wire may be attached to the bonding pad while the position directly below the bonding pad is supported by the first reflecting part.

Thus, adding the first reflecting part to the light-emitting element makes it possible to support the position directly below the bonding pad of the light-receiving element using the first reflecting part and a jig or a similar tool. Therefore, the bonding wire can be attached to the bonding pad in a reliable manner. Also, the first reflecting part makes it possible to prevent the jig from coming into contact with the light-emitting element, and as a result, it is possible to prevent the light-emitting element from being damaged.

A third aspect of the invention relates to an optical device, characterized in comprising:

a substrate having a first surface and a second surface that is opposite the first surface;

a light-emitting element having a first center, the light-emitting element being installed on the second surface; and a light-receiving element having a second center, the light-receiving element being installed on the first surface; wherein at least a part of the light-emitting element is arranged at a position that overlaps the light-receiving element with respect to a plan view;

the light-receiving element installed subsequent to the light-emitting element has a bonding pad;

the bonding pad is provided at a position that is displaced relative to the second center towards a first direction with respect to the plan view; and the first center is provided at a position that is displaced relative to the second center towards a second direction, which is opposite the first direction, with respect to the plan view.

According to the third aspect of the invention, the bonding pad of the light-receiving element is provided to the position that is displaced relative to a center of the light-receiving element (i.e., the second center) towards the first direction with respect to the plan view, and a center of the light-emitting element (i.e., the first center) is displaced relative to the center of the light-receiving element (i.e., the second center) towards the second direction with respect to the plan view. Therefore, the bonding wire can be attached to the bonding pad in a reliable manner.

According to a fourth aspect of the invention, the light-emitting element may have a rectangular profile with respect to the plan view; wherein one side of the rectangle may be tangent to a circle having a given radius and having a center on the bonding pad with respect to the plan view.

Thus, the light-emitting element may be separated from the position directly below the bonding pad of the light-receiving element by the given radius. Therefore, a space can be created at the position directly below the bonding pad of the light-receiving element.

According to a fifth aspect of the invention, the light-emitting element may have a rectangular profile with respect to the plan view; wherein one side of the rectangle may be perpendicular to a direction in which the first center and the second center are connected, with respect to the plan view.

Thus, the light-emitting element can be separated from the position directly below the bonding pad of the light-receiving element in an effective manner. Therefore, a space can be created at the position directly below the bonding pad of the light-receiving element.

According to a sixth aspect of the invention, the entirety of the light-emitting element may be arranged at a position at which there is a complete overlapping of the light-receiving element with respect to the plan view.

Thus, the light-emitting element completely overlaps the light-receiving element with respect to the plan view, and whereby light can readily reach the light-receiving element. Specifically, a light-blocking region formed by the light-emitting element overlaps a light-blocking region formed by the light-receiving element, and a light-blocking region as a whole corresponds only to the light-blocking region formed by the light-receiving element.

According to a seventh aspect of the invention, the optical device may further comprise a first reflecting part for reflecting light emitted by the light-emitting element, the first reflecting part having a third center, wherein the third center may coincide with the first center with respect to the plan view.

Thus adding the first reflecting part to the light-emitting element makes it possible to support the position directly below the bonding pad of the light-receiving element with the first reflecting part and a jig or a similar tool. Therefore, the bonding wire can be attached to the bonding pad in a reliable manner.

An eighth aspect of the invention relates to a biological information detector, characterized in comprising:

the optical device described above;

a contact part formed from a material that is transparent with respect to a wavelength of light emitted by the light-emitting element, the contact part having a contact surface in contact with a test subject; and a second reflecting part for reflecting light having biological information; wherein the light-emitting element emits light directed at a detection site of the test subject;

the light-receiving element receives light having biological information, the light being light emitted by the light-emitting element and reflected at the detection site;

the substrate is a flexible substrate formed from a material that is transparent with respect to the wavelength of light emitted by the light-emitting element; and the biological information is a pulse rate.

According to the eighth aspect, applying an optical device to a biological information detector makes it possible to provide a biological information detector (i.e., a pulse rate monitor) in which, when the bonding wire is attached to the bonding pad, the attaching can be performed.

BRIEF DESCRIPTION OF THE DRAWINGS

FIGS. 15A and 15B are examples of an outer appearance of a biological information measuring device comprising the biological information detector.

DETAILED DESCRIPTION OF EXEMPLARY EMBODIMENTS

A description shall now be given for the present embodiment. The present embodiment described below is not intended to unduly limit the scope of the claims of the present embodiment. Not every configuration described in the present embodiment is necessarily an indispensible constituent feature of the invention.

1. Optical device

Figure 1A:
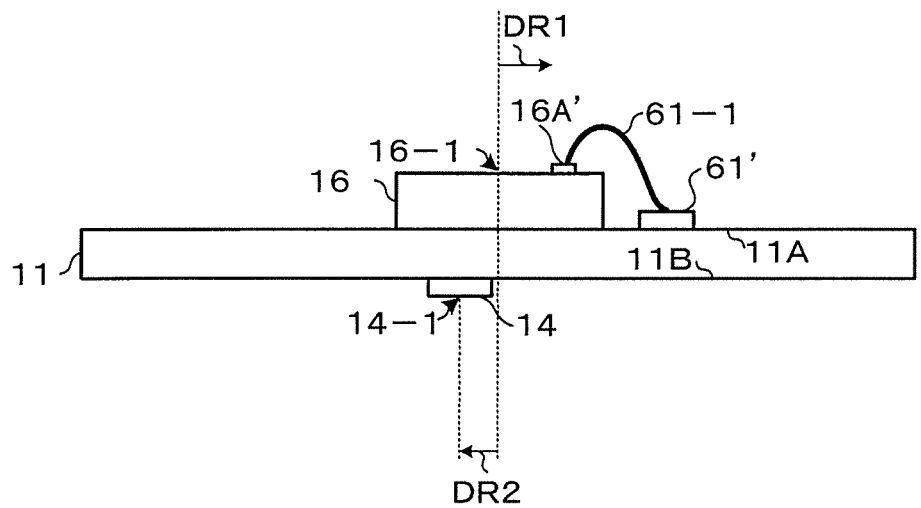
FIGS. 1A and 1B are an example of a configuration of an optical device according to a present embodiment.
Figure 1B:
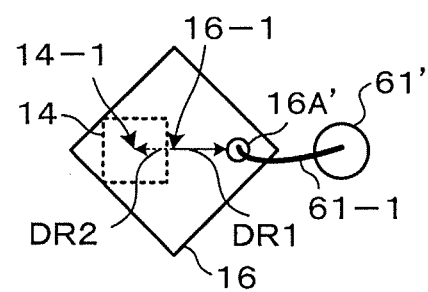

FIGS. 1A and 1B are an example of a configuration of an optical device according to a present embodiment. In FIGS. 1A and 1B, the dimensions of each of the members are not intended to accurately represent actual dimensions. Specifically, in FIGS. 1A and 1B, the dimensions of each of the members have been expanded or reduced in order to facilitate understanding of the descriptions given below. Similarly, drawings other than FIGS. 1A and 1B are not intended to necessarily represent actual dimensions.

FIG. 1A shows a cross-section view, and FIG. 1B shows a plan view. As shown in FIG. 1A, the optical device comprises a substrate 11, a light-emitting element 14, and a light-receiving element 16. The substrate 11 has a first surface 11A and a second surface 11B that is opposite the first surface 11A. The light-emitting element 14 is installed on the first surface 11B, and the light-receiving element 16 is installed on the second surface 11A. As shown, e.g., on FIG. 1B, the light-emitting element 14 has a first center 14-1 and the light-receiving element 16 has a second center 16-1 with respect to the plan view.

In the example shown in FIGS. 1A and 1B, the entirety of the light-emitting element 14 is arranged in a position that completely overlaps the light-receiving element 16 with respect to the plan view. However, at least a part of the light-emitting element 14 may be arranged in a position that overlaps the light-receiving element 16 with respect to the plan view. Specifically, with respect to the plan view, the light-emitting element 14 falls within the light-receiving element 16, but a part of the light-emitting element 14 may protrude from the light-receiving element 16 with respect to the plan view.

Although in the example shown in FIGS. 1A and 1B, both of the light-emitting element 14 and the light-receiving element 16 are already attached to the substrate 11, in reality, the light-receiving element 16 is attached to the substrate 11 in a state in which the light-emitting element 14 has been attached to the substrate 11. The light-receiving element 16, which is installed after the light-emitting element 14, has a bonding pad 16A'. The bonding pad 16A' is provided at a position that is displaced relative to the second center 16-1 towards a first direction DR1 with respect to the plan view. Also, the first center 14-1 is provided at a position that is displaced relative to the second center 16-1 towards a second direction DR2, which is opposite the first direction DR1, with respect to the plan view.

The bonding pad 16A' of the light-receiving element 16 is displaced relative to a center of the light-receiving element 16 (i.e., the second center 16-1) towards the first direction DR1 with respect to the plan view, and a center of the light-emitting element 14 (i.e., the first center 14-1) is displaced relative to the center of the light-receiving element 14 (i.e., the second center 16-1) towards the second direction DR2 with respect to the plan view. Therefore, when the bonding wire 61-1 is attached to the bonding pad 16A', a position directly below the bonding pad 16A' can be supported using a jig or a similar tool. The bonding wire 61-1 can thereby be attached in a reliable manner.

In the example shown in FIGS. 1A and 1B, the bonding wire 61-1 provides an electrical connection between the bonding pad 16A' of the light-receiving element 16 and a pad 61' for providing a connection to the light-receiving element 16 (or in a broader sense, wiring for the light-receiving element 16). Also, examples of configurations of the optical device are not limited by that shown in FIGS. 1A and 1B, and the shape, or a similar attribute, of a part of the example of configuration (e.g., the light-emitting element 14, the light-receiving element 16, the bonding pad 16A', and other components) may be modified.

1.1 Method for Manufacturing Optical Device

Figure 2A:
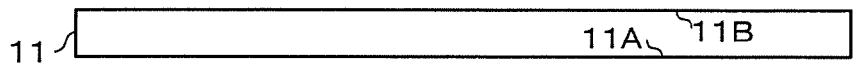
FIGS. 2A, 2B, 2C, and 2D are an example of steps according to a method for manufacturing the optical device of the present embodiment.

FIGS. 2A, 2B, 2C, and 2D are an example of steps according to a method for manufacturing the optical device of the present embodiment. While in the example shown in FIGS. 1A and 1B, both of the light-emitting element 14 and the light-receiving element 16 are already attached to the substrate 11, as shown in FIG. 2A, the substrate 11 having a first surface 11A and a second surface 11B that is opposite the first surface 11A is readied. In an instance in which the first surface 11A refers to, e.g., a front surface, and the second surface 11B refers to, e.g., a reverse surface, in the example shown in FIG. 2A, the substrate 11 is upside down.

Figure 2B:
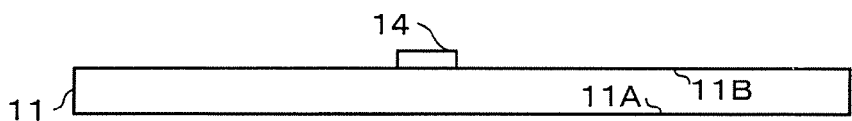
Figure 2C:
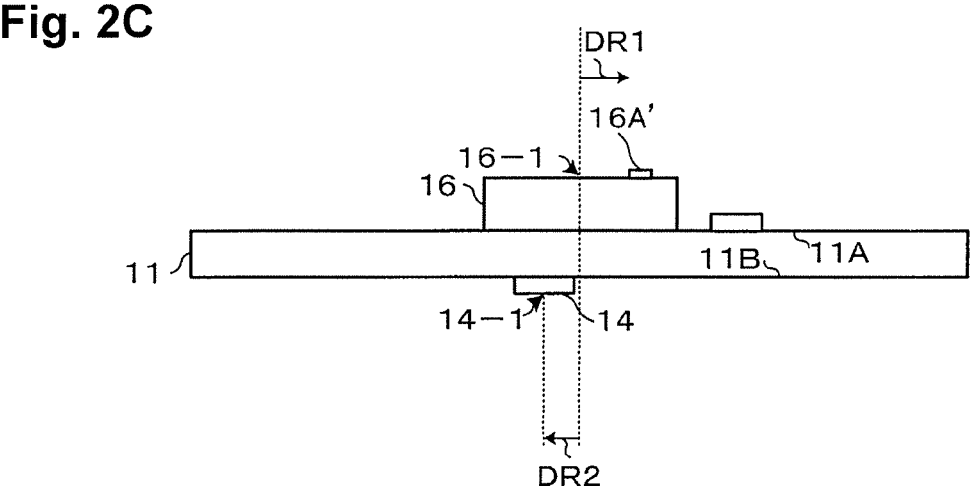

As shown in FIG. 2B, the light-emitting element 14 is installed on the second surface 11B. Then, the substrate 11 to which the light-emitting element 14 is attached is turned over, and the light-receiving element 16 is installed on the first surface 11A. As shown in FIG. 2C, the following conditions (a) through (c) are satisfied (see FIG. 1B).

(a) The light-receiving element 16 having the second center 16-1 and the bonding pad 16A' overlaps with at least a part of the light-emitting element 14 with respect to a plan view;

(b) the bonding pad 16A' is displaced relative to the second center 16-1 towards the first direction DR1 with respect to the plan view; and (c) the first center 14-1 is displaced relative to the second center 16-1 towards the second direction DR2 with respect to the plan view.

Figure 2D:
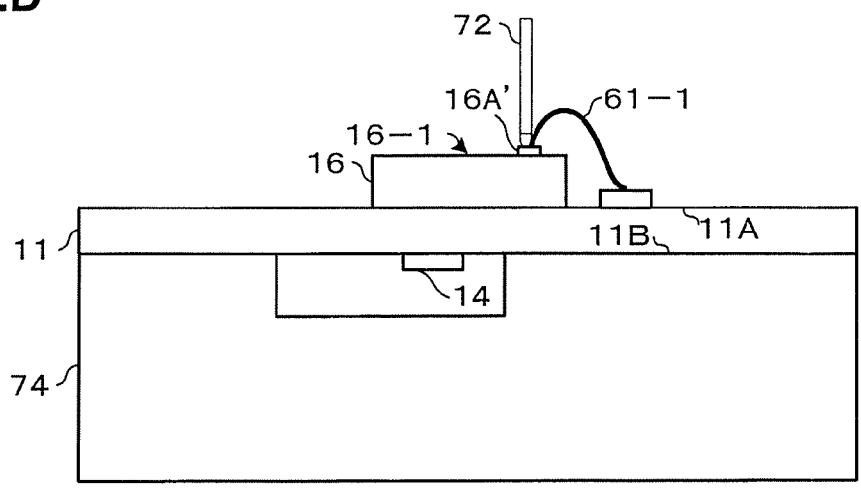

As shown in FIG. 2D, a position directly below the bonding pad 16A' of the light-receiving element 16 can be supported by a jig 74. Since the position directly below the bonding pad 16A' of the light-receiving element 16 is being supported, even when the bonding pad 16A' is restrained with a bonding tool 72, the bonding pad 16A' of the light-receiving element 16 can be immobilized.

Figure 3:
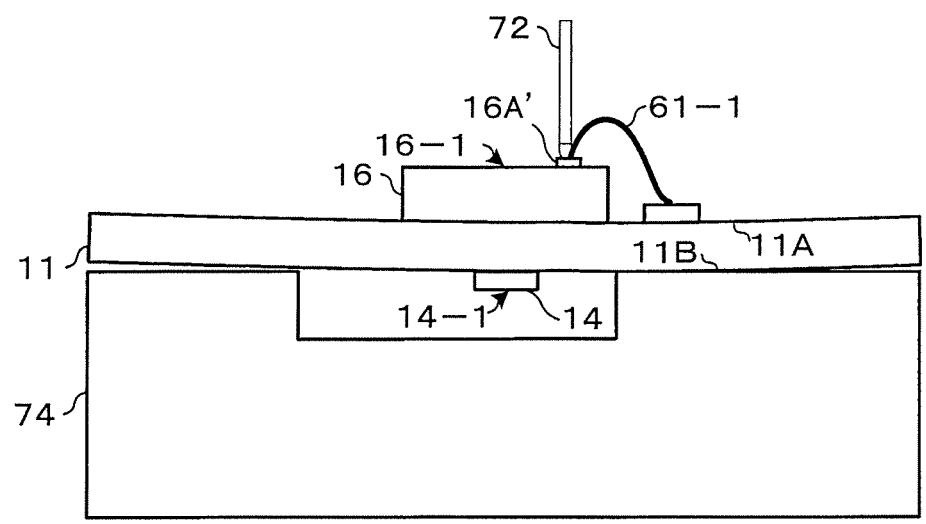
FIG. 3 is a comparative example of an optical device.

FIG. 3 is a comparative example of an optical device. In the example shown in FIG. 3, the above-mentioned condition (c) is not satisfied. As shown in FIG. 3, the jig 74 must provide a space at a position directly below the bonding pad 16A' of the light-receiving element 16 so that the light-emitting element 14 is not destroyed. Therefore, the position directly below the bonding pad 16A' of the light-receiving element 16 cannot be directly supported by the jig 74. Since the position directly below the bonding pad 16A' of the light-receiving element 16 is not supported, when the bonding pad 16A' is restrained using the bonding tool 72, the substrate 11 is caused to bend. The position of the bonding pad 16A' of the light-receiving element 16 changes with the bending of the substrate 11. Since the bonding pad 16A' cannot be immobilized, the bonding wire 61-1 cannot be attached to the bonding pad 16A' in a reliable manner.

In contrast to the example shown in FIG. 3, in the example shown in FIG. 2D, the bonding wire 61-1 is attached to the bonding pad 16A' while the position directly below the bonding pad 16A' is supported. Thus, in the example shown in FIG. 2D, the bonding wire 61-1 can be attached to the bonding pad 16A' in a reliable manner. As a result, in the method for manufacturing the optical device in which the bonding wire 61-1 is attached to the bonding pad 16A', the attaching can be performed more reliably.

Figure 4A:
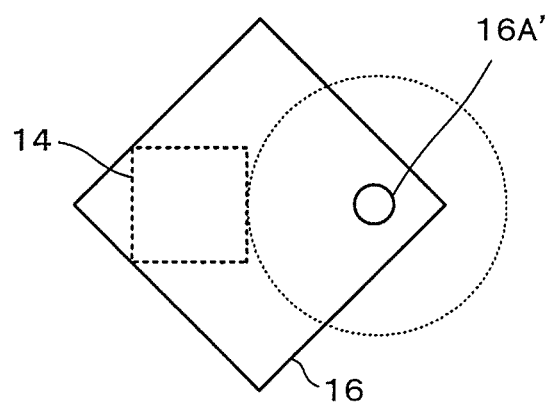
FIGS. 4A and 4B are examples of an arrangement of the optical device.
Figure 4B:
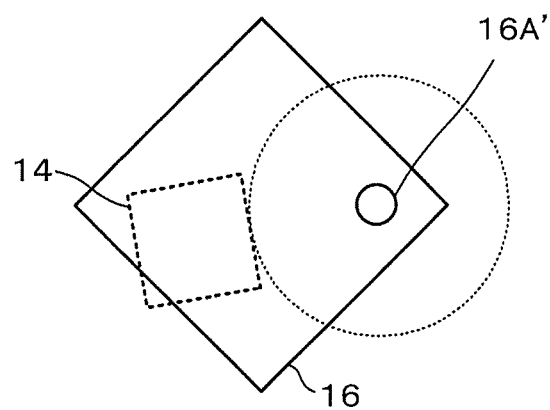

FIGS. 4A and 4B are examples of an arrangement of the optical device. As with FIG. 1B, in the example shown in FIG. 4A and the example shown in FIG. 4B, the light-emitting element 14 and the light-receiving element 16 are shown as an optical device. As shown in FIGS. 4A and 4B, the light-emitting element 14 has a rectangular profile with respect to the plan view, and one side of the rectangle is tangent to a circle having a given radius and having a center on the bonding pad 16A' (or in a narrower sense, a center of the bonding pad 16A') with respect to the plan view. The light-emitting element 14 can be separated, by the given radius, from the position directly below the bonding pad 16A' of the light-receiving element 16. Therefore, a space can be created at the position directly below the bonding pad 16A' of the light-receiving element 16. For example, as shown, e.g., in FIG. 2D, the substrate 11 can be directly supported by the jig 74.

The given radius of the circle having a center on the bonding pad 16A' shown in FIG. 4A is equal to the given radius of the circle having a center on the bonding pad 16A' shown in FIG. 4B, and the light-emitting element 14 can be separated from the position directly below the bonding pad 16A' of the light-receiving element 16 by the same given radius. While in the example shown in FIG. 4A, the light-emitting element 14 completely overlaps the light-receiving element 16 with respect to the plan view, in the example shown in FIG. 4B, a part of the light-emitting element 14 overlaps the light-receiving element 16 with respect to the plan view. In an instance in which light emitted by the light-emitting element 14 is transmitted through the substrate 11 and received by the light-receiving element 16, the light-emitting element 14 with respect to the plan view forms a light-blocking region, and the light-receiving element 16 with respect to the plan view also forms a light-blocking region. In the example shown in FIG. 4A, a light-blocking region as a whole corresponds only to the light-blocking region of the light-receiving element 16. In the example shown in FIG. 4B, the light-blocking region as a whole corresponds to, in addition to the light-blocking region of the light-receiving element 16, the light-blocking region of the light-emitting element 14 that protrudes from the light-blocking region of the light-receiving element 16 (i.e., the light-blocking region of the light-emitting element 14 that does not overlap with the light-blocking region of the light-receiving element 16). The light-blocking region as a whole in the example shown in FIG. 4A is smaller than the light-blocking region as a whole in the example shown in FIG. 4B. Therefore, in the example shown in FIG. 4A, light can more readily reach the light-receiving element 16 compared to the example shown in FIG. 4B.

Figure 5A:
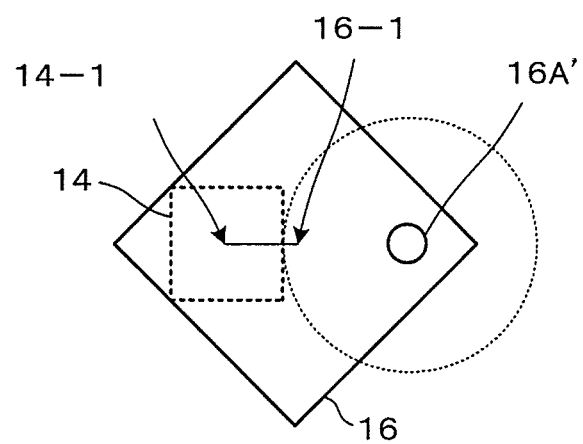
FIGS. 5A and 5B are schematic diagrams showing a distance between a first center and a second center.
Figure 5B:
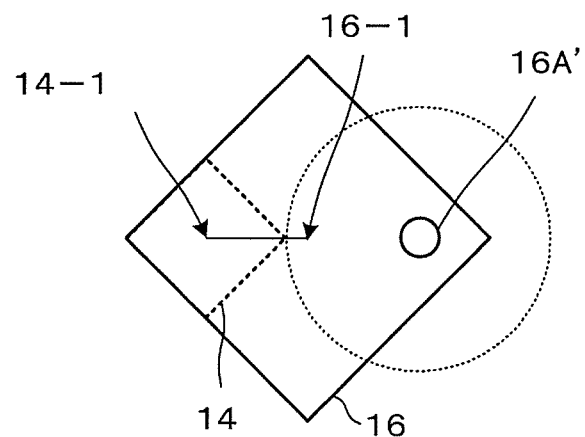

FIGS. 5A and 5B are schematic diagrams showing a distance between the first center 14-1 and a second center 16-1. As shown in FIGS. 5A and 5B, the light-emitting element 14 has a rectangular (or in a narrower sense, a square) profile with respect to the plan view, and the length of one side of a square shown in FIG. 5A is equal to the length of one side of a square shown in FIG. 5B. In the example shown in FIG. 5A, one side (e.g., a side that is nearest to the bonding pad 16A') of the square (or in a broader sense, a rectangle) is perpendicular to a direction that connects the first center 14-1 and the second center 16-1 with respect to the plan view. In the example shown in FIG. 5B, no side, i.e., none of the four sides, of the square (or in a broader sense, the rectangle) is perpendicular to the direction that connects the first center 14-1 and the second center 16-1 with respect to the plan view.

The given radius of the circle having a center on the bonding pad 16A' shown in FIG. 5A can be made smaller than the given radius of the circle having a center on the bonding pad 16A' shown in FIG. 5B. Thus, in an instance in which one side of the rectangle that represents the profile of the light-emitting element 14 is perpendicular to the direction that connects the first center 14-1 and the second center 16-1 with respect to the plan view, the distance between the first center 14-1 and the second center 16-1 can be decreased. In an instance in which light emitted by the light-emitting element 14 is transmitted through the substrate 11 and received by the light-receiving element 16, the light-receiving element 16 can receive light more effectively with a shorter distance between the first center 14-1 and the second center 16-1.

2. Biological Information Detector

Figure 6A:
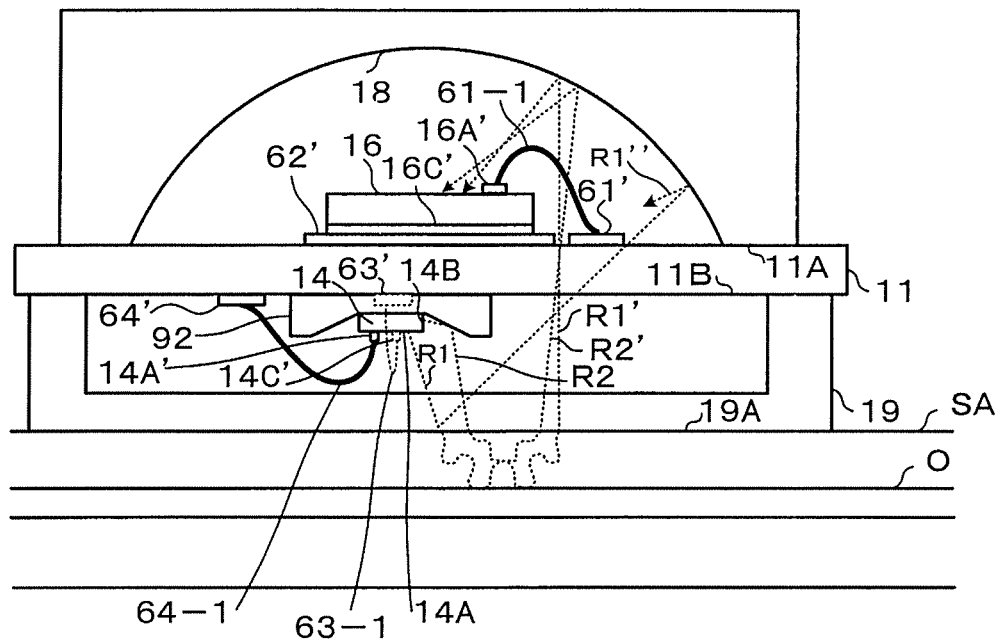
FIGS. 6A and 6B are examples of a configuration of a biological information detector according to the present embodiment.
Figure 6B:
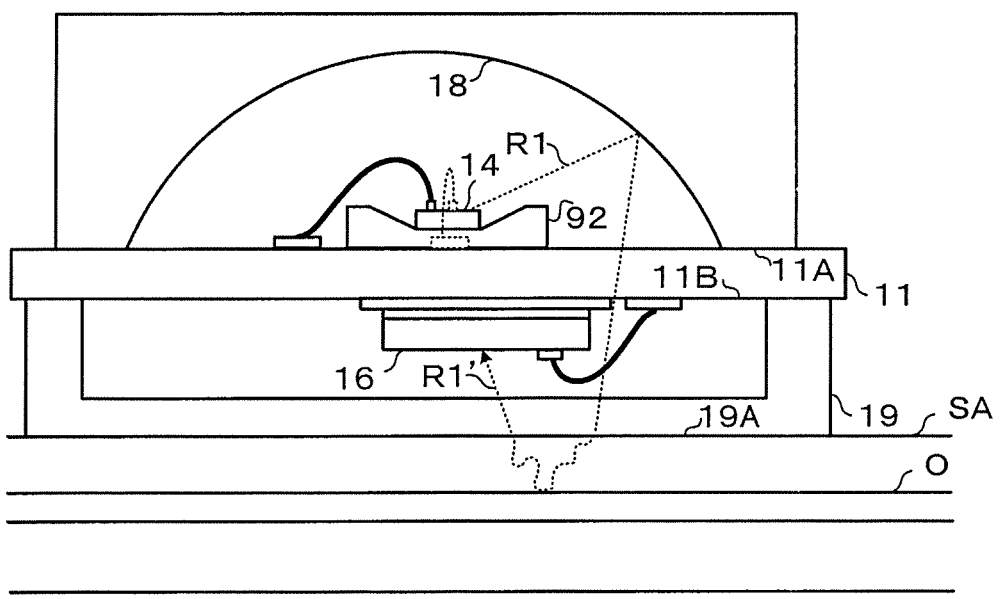

FIGS. 6A and 6B are examples of a configuration of a biological information detector according to the present embodiment. As shown in FIGS. 6A and 6B, the biological information detector comprises the optical device shown, e.g., in FIG. 1A. FIGS. 6A and 6B can also be said to show other examples of a configuration of the optical device according to the present embodiment. As shown in FIGS. 6A and 6B, the biological information detector (or in a broader sense, the optical device) may further comprise a first reflecting part 92. Structures that are identical to those in the example described above are affixed with the same numerals, and a description of the structures is not provided.

While in FIG. 6A, the light-emitting element 14 is arranged on a side towards a detection site O of a test subject (e.g., a user), in FIG. 6B, the light-receiving element 16 is arranged on a side towards the detection site O of the test subject. All of the light-receiving element 16 and other components arranged on the first surface 11A of the substrate 11 in FIG. 6A are arranged on the second surface 11B of the substrate 11 in FIG. 6B; however, 16A' and other numerals shown in FIG. 6A are not shown in FIG. 6B. Also, all of the light-emitting element 14 and other components arranged on the second surface 11B of the substrate 11 in FIG. 6A are arranged on the first surface 11A of the substrate 11 in FIG. 6B; however, 14A and other numerals shown in FIG. 6A are not shown in FIG. 6B. Also, the light-emitting element 14 in FIG. 6A emits a first light R1 and a second light R2; however, the second light R2 is not shown in FIG. 6B.

The light-emitting element 14 emits light R1 directed at the detection site O of the test subject (e.g., the user). The light-emitting element 14 also emits the second light R2 directed at a direction other than that of the detection site O (i.e., directed at the first reflecting part 92). The first reflecting part 92 reflects the second light R2 towards the detection site O. The light-receiving element 16 receives light R1' (i.e., reflected light) having biological information, the light R1' being light R1 emitted by the light-emitting element 14 reflecting at the detection site O. The light-receiving element 16 also receives light R2' (i.e., reflected light) having biological information, the light R2' being the second light R2 reflecting at the detection site O.

The biological information detector (or in a broader sense, the optical device) may further comprise a second reflecting part 18. In the examples shown in FIGS. 6A and 6B, the second reflecting part 18 reflects the light R1 emitted by the light-emitting element 14 or the light R1' (i.e., reflected light) having biological information. In the example shown in FIG. 6A, the second reflecting part 18 reflects the light R1' and R2' (i.e., reflected light) having biological information from the detection site O towards the light-receiving element 16. In FIG. 6B, the second reflecting part 18 reflects the light R1 emitted by the light-emitting element 14 towards the detection site O. The second reflecting part 18 may have a reflecting surface on a dome surface provided between the light-emitting element 14 and the light-receiving element 16.

The biological information detector (or in a broader sense, the optical device) may further comprise a contact part 19. The contact part 19 has a surface 19A that comes into contact with the test subject, and is formed from a material that is transparent with respect to the wavelength of the light R1 emitted by the light-emitting element 14 (e.g., glass). The substrate 11 is also formed from a material that is transparent with respect to the wavelength of the light R1 emitted by the light-emitting element 14 (e.g., polyimide), and the substrate 11 is formed from, e.g., a flexible substrate.

In the example shown in FIGS. 6A and 6B, the detection site O (e.g., a blood vessel) is within the test subject. The first light R1 travels into the test subject and diffuses or scatters at the epidermis, the dermis, and the subcutaneous tissue. The first light R1 then reaches the detection site O, and is reflected at the detection site O. The reflected light R1' reflected at the detection site O diffuses or scatters at the subcutaneous tissue, the dermis, and the epidermis. In FIG. 6A, the reflected light R1' travels to the reflecting part 18. In FIG. 6B, the first light R1 travels to the detection site O via the second reflecting part 18. The first light R1 is partially absorbed at the blood vessel. Therefore, due to an effect of a pulse, the rate of absorption at the blood vessel varies, and the amount of the reflected light R1' reflected at the detection site O also varies. Biological information (e.g. pulse rate) is thus reflected in the reflected light R1' reflected at the detection site O.

In FIG. 6A, the second light R2 travels into the test subject, and the reflected light R2' reflected at the detection site O travels to the second reflecting part 18. The biological information (i.e., pulse rate) is also reflected in the reflected light R2' reflected at the detection site O.

Examples of configurations of the biological information detector (or in a broader sense, the optical device) are not limited by those shown in FIGS. 6A and 1B, and the shape, or a similar attribute, of a part of the example of configuration (e.g., the first reflecting part 92, the second reflecting part 18, and other components) may be modified. The biological information may also be blood oxygen saturation level, body temperature, heart rate, or a similar variable; and the detection site O may be positioned at a surface SA of the test subject. In the example shown in FIG. 6A, the first light R1 and the second light R2 are each shown by a single line, and in the example shown in FIG. 6B, the first light R1 is shown by a single line; however, in reality, the light-emitting element 14 emits many light beams in a variety of directions.

In the example shown in FIG. 6A, a part of the wiring for the light-receiving element 16 is shown, and the pad 61' for providing a connection to the light-receiving element 16 is shown. The bonding pad 16A' (or in a broader sense, an electrode) is, e.g., an anode of the light-receiving element 16. In the example shown in FIG. 6A, a connecting part 62' for providing a connection to, e.g., an electrode pad 16C' (or in a broader sense, an electrode) of the light-receiving element 16 is also shown as a part of the wiring for the light-receiving element 16. The electrode pad 16C' is, e.g., a cathode of the light-receiving element 16. In the example shown in FIG. 6A, the connecting part 62' is directly connected to an electrode pad 16C'.

Also, in the example shown in FIG. 6A, a part of the wiring for the light-emitting element 14 is shown, and a pad 64' for providing a connection to the light-emitting element 14 is shown. The connecting pad 64' is connected to a bonding pad 14A' (or in a broader sense, an electrode) of the light-emitting element 14 via a bonding wire 64-1. The bonding pad 14A' is, e.g., an anode of the light-emitting element 14. The example shown in FIG. 6A shows a cross-section view corresponding to one cut plane. In the example shown in FIG. 6A, a connecting pad 63' that is not, in reality, present on the cut plane is represented by a dotted line. The connecting pad 63' is connected to a bonding pad 14C' (or in a broader sense, an electrode) of the light-emitting element 14 via a bonding wire 63-1. The bonding pad 14C' is, e.g., a cathode of the light-emitting element 14.

Figure 7A:
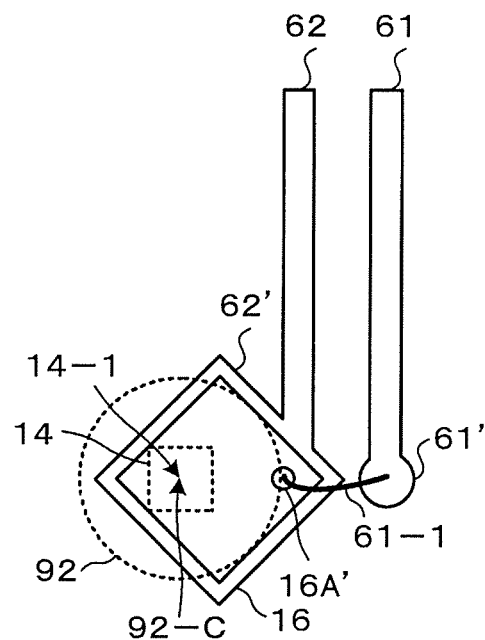
FIGS. 7A and 7B are plan views showing the biological information detector of FIG. 6A.
Figure 7B:
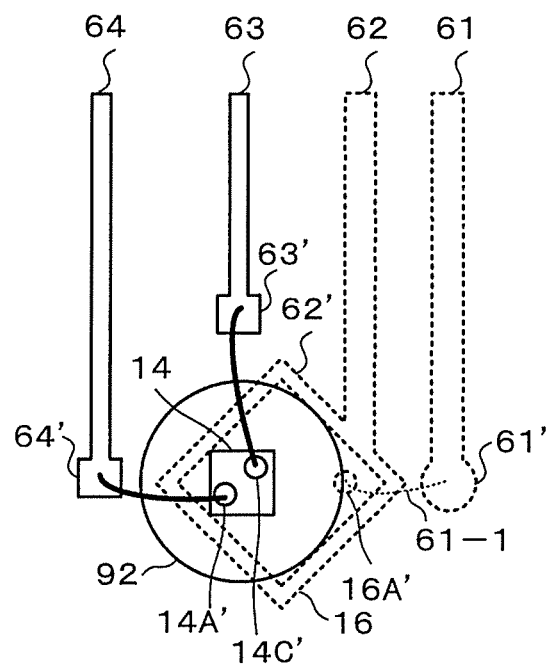

FIGS. 7A and 7B are plan views showing the biological information detector (or in a broader sense, the optical device) of FIG. 6A. FIG. 7A corresponds to a plan view of a side towards the light-receiving element 16, and FIG. 7B corresponds to a plan view of a side towards the light-emitting element 14. Structures that are identical to those in the examples described above are affixed with the same numerals, and a description of the structures is not provided.

In FIG. 7A, each of the light-emitting element 14 and the first reflecting part 92 is shown by a dotted line. As shown in FIG. 7A, the first reflecting part 92 has a third center 92-C, and the third center 92-C coincides with the first center 14-1 of the light-emitting element 14 with respect to the plan view. In an instance in which the third center 92-C coincides with the first center 14-1, the first reflecting part 92 is capable of reflecting light emitted by the light-emitting element 14 in an efficient manner. The example shown in FIG. 7A satisfies a positional relationship shown in FIG. 1B. Therefore, the third center 92-C (i.e., the first center 14-1) is provided at a position that is displaced, relative to the second center 16-1, towards the second direction DR2, which is opposite the first direction DR1, with respect to the plan view.

As shown in FIG. 7A, a wiring 61 for the light-receiving element 16 has a connecting pad 61' and the bonding wire 61-1 at one end. Also, a wiring 62 for the light-receiving element 16 has the connecting part 62' at one end. As shown in FIG. 7B, a wiring 63 for the light-emitting element 14 has the connecting pad 63' and the bonding wire 63-1 at one end. Also, a wiring 64 for the light-emitting element 14 has the connecting pad 64' and the bonding wire 64-1 at one end. Electrical power can be fed to the light-emitting element 14 from the wiring 63 and the wiring 64, and an electrical signal from the light-receiving element 16 can be extracted from wiring 63 and the wiring 64. In FIG. 7A, the wiring 63 and the wiring 64 are not shown. In FIG. 7B, the light-receiving element 16 and similar components are each shown by a dotted line.

The configuration of the wiring 63 and the wiring 64 for the light-emitting element 14 and the wiring 61 and the wiring 62 for the light-receiving element 16 are not limited by the examples shown in FIGS. 7A and 7B. For example, the shape of the connecting pad 61' of the wiring 61 may, instead of being circular as shown in FIG. 7A, be, e.g., square, elliptical, polygonal, or describing another shape. The shape of, e.g., the connecting pad 63' of the wiring 63 may, instead of being square as shown in FIG. 7B, also be, e.g., circular, elliptical, polygonal, or describing another shape.

2.1 Method for Manufacturing Optical Device in Biological Information Detector

Figure 8A:
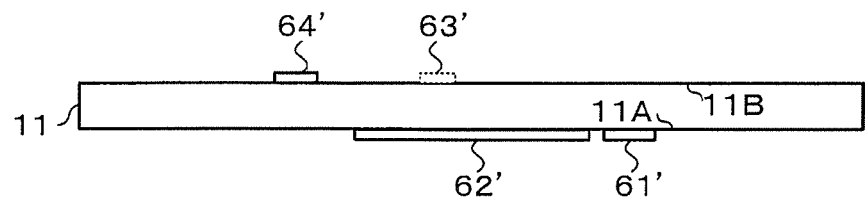
FIGS. 8A, 8B, 8C, and 8D are another example of steps according to the method for manufacturing the optical device of the present embodiment.
Figure 8B:
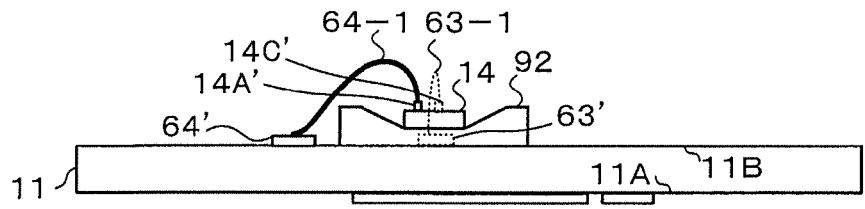
Figure 8C:
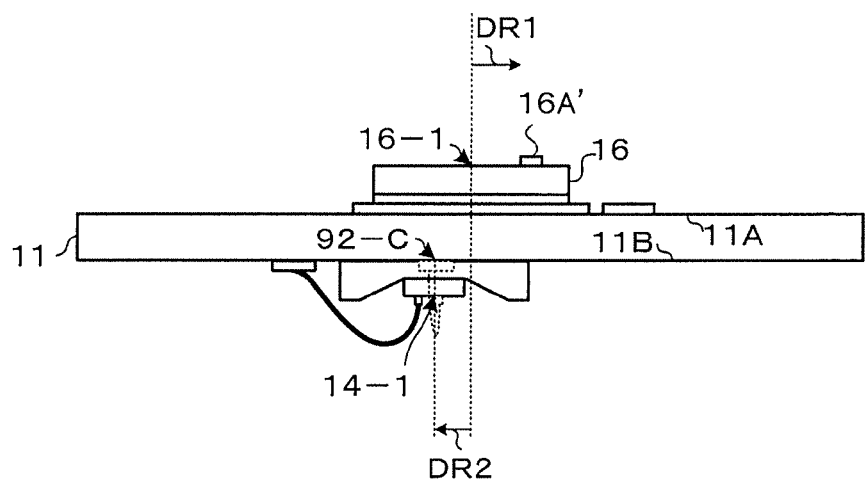
Figure 8D:
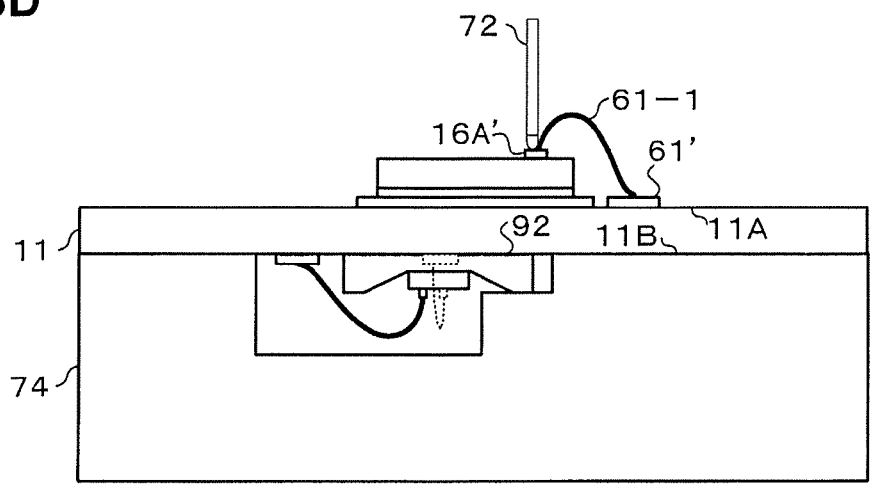

FIGS. 8A, 8B, 8C, and 8D are another example of steps according to the method for manufacturing the optical device of the present embodiment. Structures that are identical to those in the examples described above are affixed with the same numerals, and a description of the structures is not provided. The example differs, in general, from the example shown in FIG. 2D in that the light-emitting element 14 is installed on the second surface 11B with the first reflecting part 92 for reflecting light emitted by the light-emitting element 14 interposed therebetween, and the bonding wire 61-1 is attached to the bonding pad 16A' while the position directly below the bonding pad 16A' is supported by the first reflecting part 92 (FIG. 8D).

Adding the first reflecting part 92 to the light-emitting element 14 makes it possible to support the position directly below the bonding pad 16A' of the light-receiving element 16 using the first reflecting part 92 and the jig 74 or a similar tool. Therefore, the bonding wire 16-1 can be attached to the bonding pad 16A' in a reliable manner. Also, the first reflecting part 92 makes it possible to prevent the jig 74 from coming into contact with the light-emitting element 14, and as a result, it is possible to prevent the light-emitting element 14 from being damaged.

As shown in FIGS. 8A, 6A, and 7B, the connecting pad 64' and the connecting pad 63' (or in a broader sense, the wirings 64, 63 for the light-emitting element 14) are arranged in advance on the second surface 11B of the substrate 11. Also, the connecting pad 61' and the connecting part 62' (or in a broader sense, the wirings 61, 62 for the light-receiving element 16) are arranged in advance on the first surface 11A of the substrate 11.

As shown in FIG. 8B, the first reflecting part 92, to which the light-emitting element 14 has been attached in advance, is arranged on the second surface 11B of the substrate 11, and the bonding wire 64-1 is attached to the bonding pad 14A' while the first surface 11A of the substrate 11 is supported a jig or a similar tool (not shown). Also, the bonding wire 63-1 is attached to the bonding pad 14C'.

As shown in FIG. 8C, the following conditions (a) through (c) are satisfied.

(a) The light-receiving element 16 having the second center 16-1 and the bonding pad 16A' overlaps with at least a part of the light-emitting element 14 with respect to the plan view;

(b) the bonding pad 16A' is displaced relative to the second center 16-1 towards the first direction DR1 with respect to the plan view; and (c) the third center 92-C (and the first center 14-1) are displaced relative to the second center 16-1 towards a second direction DR2 with respect to the plan view.

As shown in FIG. 8C, when a wire bonding step in the optical device is complete, the second reflecting part 18 and the contact part 19 are attached to the substrate 11 as shown, e.g., in FIG. 6A.

As shown in FIG. 6A or FIG. 6B, the substrate 11 is arranged between the second reflecting part 18 and the contact part 19. Therefore, even in an instance in which the light-emitting element 14 and the light-receiving element 16 are arranged on the substrate 11, there is no need to separately provide a mechanism for supporting the substrate 11 itself, and the number of components is smaller. Also, since the substrate 11 is formed from a material that is transparent with respect to the emission wavelength, the substrate 11 can be arranged on a light path from the light-emitting element 14 to the light-receiving element 16, and there is no need to accommodate the substrate 11 at a position away from the light path, such as within the second reflecting part 18. A biological information detector (or in a broader sense, an optical device) that can be readily assembled can thus be provided. Also, the second reflecting part 18 is capable of increasing the amount of light reaching the light-receiving element 16 or the detection site O, and the detection accuracy (i.e., the signal-to-noise ratio) of the biological information detector increases.

In Patent Citation 1, it is necessary to install the light-emitting element 11, the light-receiving element 12, the substrate 15, and the transparent material 142 in the interior of the reflecting part 131. Therefore, a small optical probe 1 cannot be assembled with ease. Also, according to paragraph [0048] in Patent Citation 1, the substrate 15 is formed so that an interior-side of the reflecting part 131 is a diffuse reflection surface. In other words, the substrate 15 in Patent Citation 1 is not required to be formed from a transparent material.

The thickness of the substrate 11 is e.g., 10 µm to 1000 µm. The substrate 11 is, e.g., a printed circuit board; however, a printed circuit board is not generally formed from a transparent material, as with the substrate 15 of Patent Citation 1. Specifically, the inventors purposefully used a configuration in which the printed circuit board is formed from a material that is transparent at least with respect to the emission wavelength of the light-emitting element 14. The thickness of the contact part 19 is, e.g., 1 µm to 3000 µm.

The light-emitting element 14 is, e.g., an LED. The light emitted by the LED has a maximum intensity (or in a broader sense, a peak intensity) within a wavelength range of, e.g., 425 nm to 625 nm, and is, e.g., green in color. The thickness of the light-emitting element 14 is, e.g., 20 µm to 1000 µm. The light-receiving element 16 is, e.g., a photodiode, and can generally be formed by a silicon photodiode. The thickness of the light-receiving element 16 is, e.g., 20 µm to 1000 µm. The silicon photodiode has a maximum sensitivity (or in a broader sense, a peak sensitivity) for received light having a wavelength within a range of, e.g., 800 nm to 1000 nm. Ideally, the light-receiving element 16 is formed by a gallium arsenide phosphide photodiode, and the gallium arsenide phosphide photodiode has a maximum sensitivity (or in a broader sense, a peak sensitivity) for received light having a wavelength within a range of, e.g., 550 nm to 650 nm. Since biological substances (water or hemoglobin) readily allow transmission of infrared light within a wavelength range of 700 nm to 1100 nm, the light-receiving element 16 formed by the gallium arsenide phosphide photodiode is more capable of reducing noise components arising from external light than the light-receiving element 16 formed by the silicon photodiode.

Figure 9:
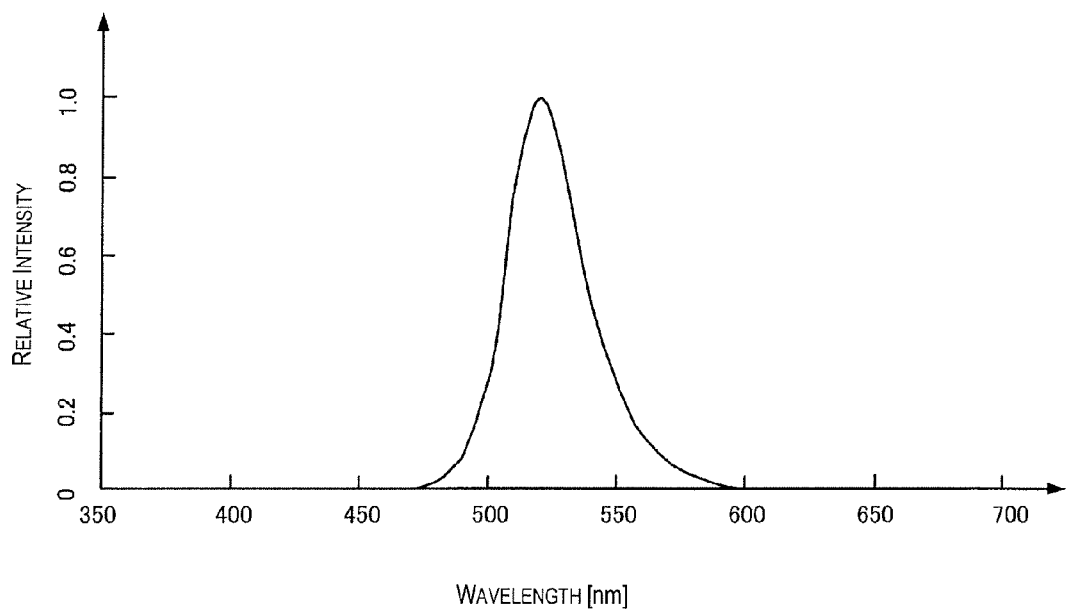
FIG. 9 is an example of intensity characteristics of light emitted by a light-emitting element.

FIG. 9 shows an example of intensity characteristics of the light emitted by the light-emitting element 14. In the example shown in FIG. 9, the intensity is at a maximum for light having a wavelength of 520 nm, and the intensity of light having other wavelengths is normalized with respect thereto. Also, in the example shown in FIG. 9, the wavelengths of light emitted by the light-emitting element 14 are within a range of 470 nm to 600 nm.

Figure 10:
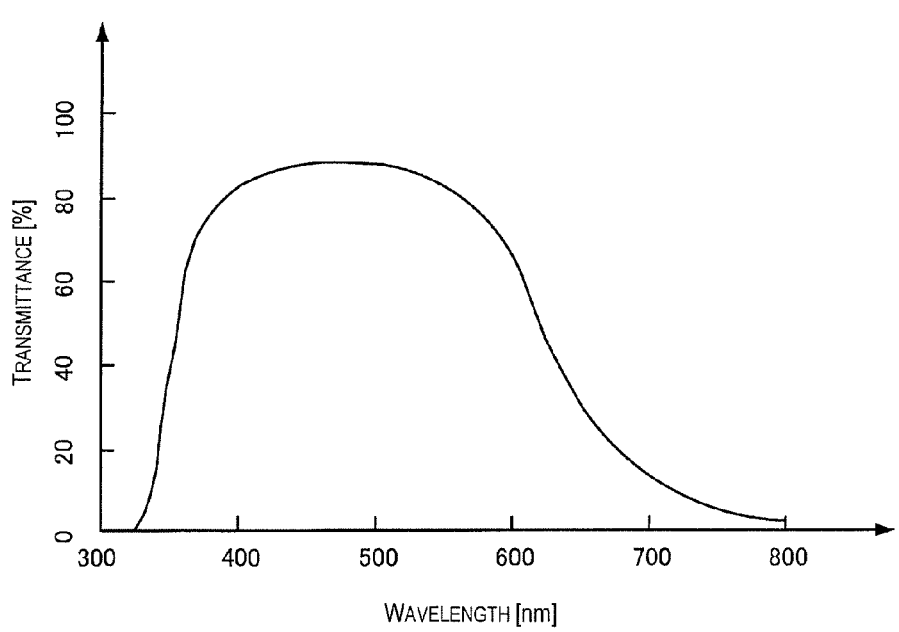
FIG. 10 is an example of transmission characteristics of light passing through a contact part.

FIG. 10 shows an example of transmission characteristics of light passing through the contact part 19. As shown in FIG. 10, at the wavelength of light (520 nm) emitted by the light-emitting element 14 at which the intensity is at a maximum shown, e.g., in FIG. 9, the transmittance is 50% or above. Also, although an example of transmission characteristics of light passing through the substrate 11 itself is not shown, transmittance of the substrate 11 with respect to a wavelength of 520 nm can be set to, e.g., 50% or above, as with the transmission characteristics shown in FIG. 10. The contact part 19 and the substrate 11 can be formed from a material that is transparent with respect to the wavelength of light R1 emitted by the light-emitting element 14.

Figure 11:
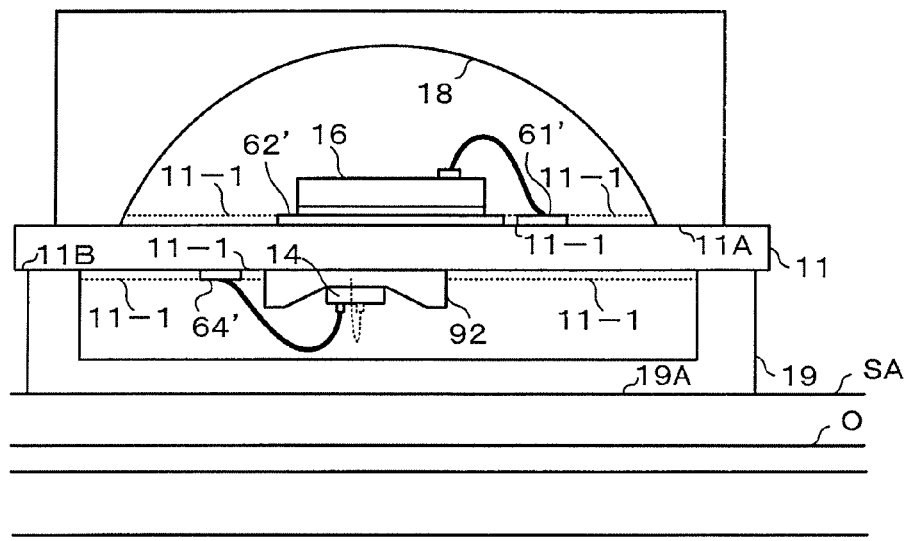
FIG. 11 is another example of a configuration of the biological information detector according to the present embodiment.

FIG. 11 is another example of a configuration of the biological information detector according to the present embodiment. As shown in FIG. 11, the light-transmitting film 11-1 can be formed on the first surface 11A and the second surface 11B, which is opposite the first surface, of the substrate 11. Structures that are identical to those in the example described above are affixed with the same numerals, and a description of the structures is not provided. The light-transmitting film 11-1 may be formed only on the first surface 11A, or may be formed only on the second surface 11B. Also, in the example shown in FIG. 11, the light-transmitting film 11-1 is formed on a light-transmitting region of the substrate 11 on which the light-emitting element 14 and the light-receiving element 16 (or in a narrower sense, the first reflecting part 92, the connecting pad 64' (i.e., wirings 63, 64 for the light-emitting element 14 in FIG. 7B), the connecting part 62', and the connecting pad 61' (i.e., wirings 61, 62 for the light-receiving element 16 in FIG. 7B)) are not arranged. Although FIG. 11 corresponds to FIG. 6A, the light-transmitting film 11-1 may be formed on at least one of the first surface 11A and the second surface 11B of the substrate 11 in FIG. 6B. The light-transmitting film 11-1 may be formed from, e.g., a solder resist (or in a broader sense, a resist).

In the example shown in FIG. 11, the first surface 11A and the second surface 11B of the substrate 11 may be processed so as to form a rough surface so that the wirings 61, 62, 63, 64 (including the connecting pads 61', 64', the connecting part 62', and similar components) on the substrate 11 do not peel off. Therefore, the light-transmitting film 11-1 is formed on the first surface 11A and the second surface 11B, whereby the roughness on the surface of the substrate 11 is filled with the light-transmitting film, and the smoothness of the entire substrate 11 is increased. Specifically, the light-transmitting film 11-1 on the substrate 11 is smooth, and can therefore reduce dispersion of light on the roughness on the surface of the substrate 11 during transmission of the light through the substrate 11. Specifically, the presence of the light-transmitting film 11-1 increases the transmittance of the substrate 11. Therefore, the amount of light reaching the light-receiving element 16 or the detection site O increases, and the detection accuracy of the biological information detector increases further.

The refractive index of the light-transmitting film 11-1 is preferably between the refractive index of air and the refractive index of the substrate 11. Further preferably, the refractive index of the light-transmitting film 11-1 is preferably closer to the refractive index of the substrate 11 than the refractive index of air. In such an instance, it is possible to reduce reflection of light on an interface.

Figure 12:
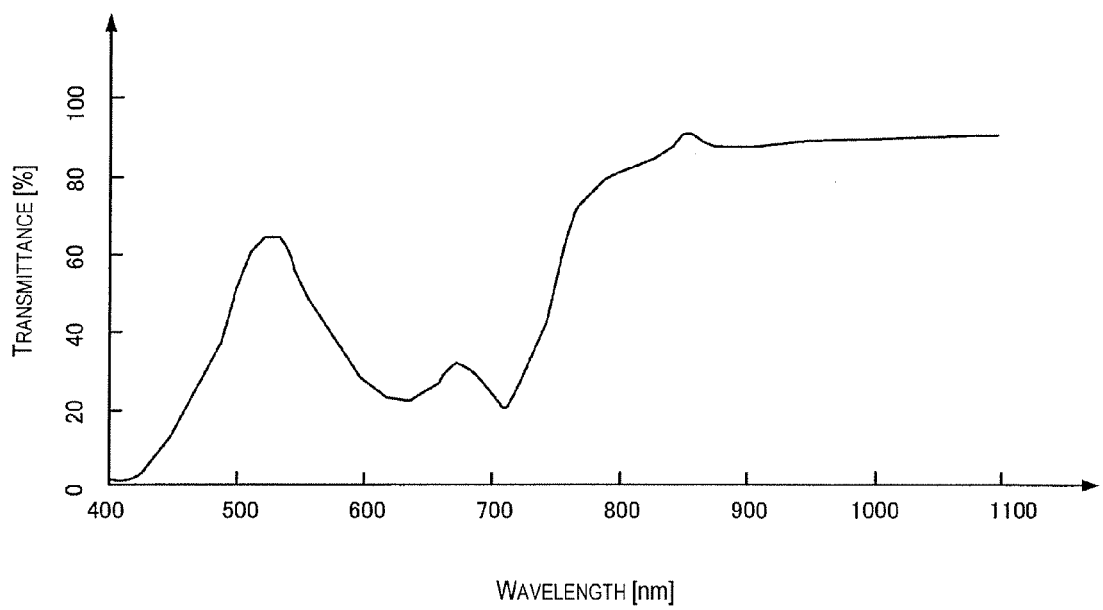
FIG. 12 is an example of transmission characteristics of light passing through a substrate coated with a light-transmitting film.

FIG. 12 is an example of transmission characteristics of light passing through the substrate 11 coated with a light-transmitting film. In the example shown in FIG. 12, transmittance is calculated using the intensity of light before being transmitted through the substrate 11 and the intensity of light after being transmitted through the substrate 11. In the example shown in FIG. 12, in the range of wavelength equal to or less than 700 nm, which is the lower limit of the optical window in biological tissue, the transmittance is at a maximum for light having a wavelength of 525 nm. Or, in the example shown in FIG. 12, in the range of wavelength equal to or less than 700 nm, which is the lower limit of the optical window in biological tissue, the wavelength of the maximum transmittance of light passing through the light transmission film 11-1 falls within a range of ±10% of the wavelength of the maximum intensity of light generated by the light-emitting part 14 in FIG. 9, for example. It is preferable that the light-transmitting film 11-1 thus selectively transmit light generated by the light-emitting element 14 (e.g., the first light R1 (or in a narrower sense, the reflected light R1' produced by the first light R1 being reflected) in FIG. 6A). The presence of the light-transmitting film 11-1 makes it possible to enhance the smoothness of the substrate 11 and prevent, to a certain extent, a decrease in efficiency of the light-emitting element 14 and the light-receiving element 16. In an instance in which transmittance has a maximum value (or in a broader sense, a peak value) within, e.g., a visible light region for light having a wavelength of 525 nm, as shown in the example in FIG. 12, the light-transmitting film 11-1 is, e.g., green.

In the example shown in FIG. 6A, the light-emitting element 14 may have a first light-emitting surface 14A that faces the detection site O and emits the first light R1. The light-emitting element 14 may also have a second light-emitting surface 14B that is a side surface of the first light-emitting surface 14A and emits the second light R2. In such an instance, the first reflecting part 92 may have a wall part that surrounds the second light-emitting surface 14B.

Figure 13A:
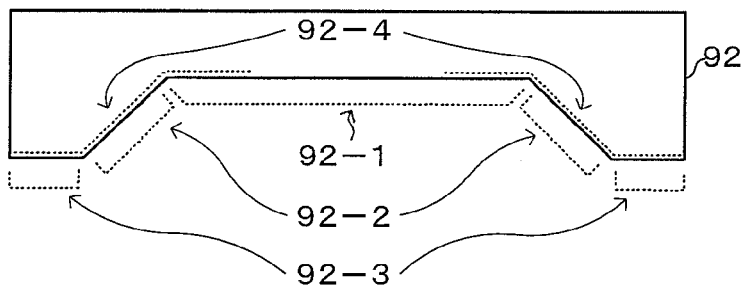
FIGS. 13A, 13B, and 13C are examples of a configuration of a first reflecting part.
Figure 13B:
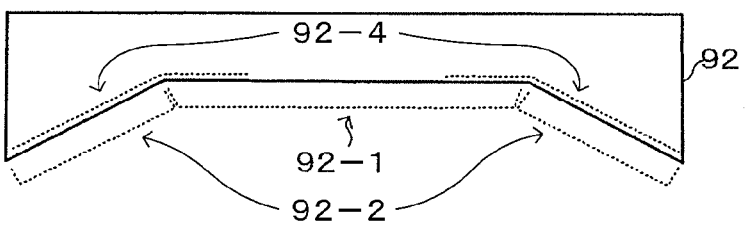
Figure 13C:
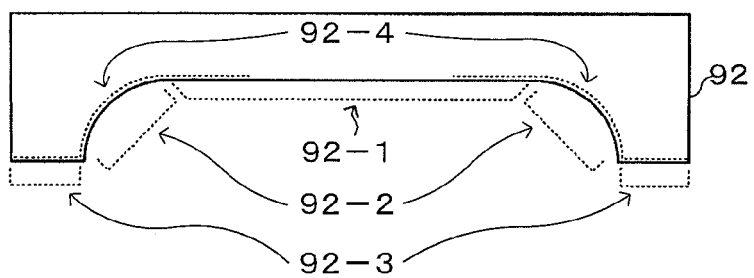

FIGS. 13A, 13B, and 13C are examples of a configuration of the first reflecting part 92 shown in FIG. 6A. As shown in FIG. 13A, the first reflecting part 92 may have a support part 92-1 for supporting the light-emitting element 14, and an inner wall surface 92-2 and a top surface 92-3 of the wall part surrounding the second light-emitting surface 14B of the light-emitting element 14. The light-emitting element 14 is not shown in FIGS. 13A through 13C. In the example shown in FIG. 13A, the first reflecting part 92 can reflect the second light R2 on the inner wall surface 92-2 towards the detection site O (see FIG. 6A), the first reflecting part 92 having a first reflecting surface on the inner wall surface 92-2. The thickness of the support part 92-1 is, e.g., 50 μm to 1000 μm, and the thickness of the wall part (92-3) is, e.g., 100 μm to 1000 μm.

In the example shown in FIG. 13A, the inner wall surface 92-2 has an inclined surface (92-2) which, with increasing distance in a width direction (i.e., a first direction) from a center of the first reflecting part 92, inclines towards the detection site O in a height direction (i.e., a direction that is perpendicular to the first direction), in cross-section view. The inclined surface (92-2) in FIG. 13A is formed by, in cross-section view, an inclined plane, but may also be a curved surface shown in, e.g., FIG. 13C, or a similar inclined surface. e inner wall surface 92-2 may also be formed as a plurality of inclined flat surfaces whose angle of inclination vary from one another, or by a curved surface having a plurality of curvatures. In an instance in which the inner wall surface 92-2 of the first reflecting part 92 has an inclined surface, the inner wall surface 92-2 of the first reflecting part 92 is capable of reflecting the second light R2 towards the detection site O. In other words, the inclined surface on the inner wall surface 92-2 of the first reflecting part 92 can be said to be the first reflecting surface for improving the directivity of the light-emitting element 14. In such an instance, the amount of light reaching the detection site O increases further. The top surface 92-3 shown in FIGS. 13A and 13C may be omitted as shown, e.g., in FIG. 13B. In an instance in which the first reflecting part 92 has the top surface 92-3, the top surface 92-3 may be supported by the jig 74 (see FIG. 8D). In FIGS. 13A through 13C, a range indicated by label 92-4 function as a mirror surface part.

Figure 14A:
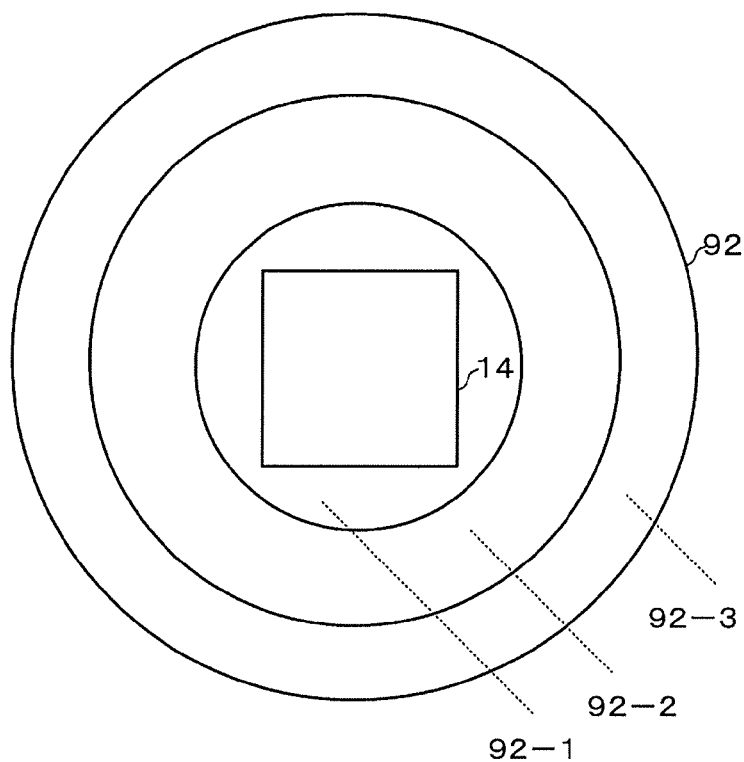
FIGS. 14A and 14B are examples of an outer appearance of the first reflecting part and the light-emitting element with respect to a plan view.
Figure 14B:
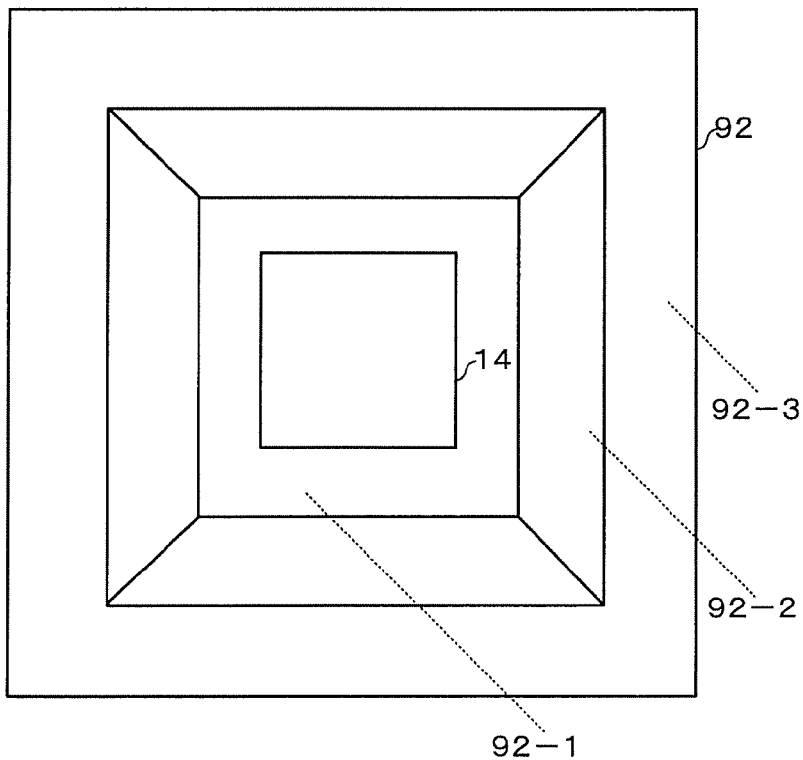

FIGS. 14A and 14B respectively show an example of an outer appearance of the first reflecting part 92 and the light-emitting element 14 of FIG. 6A in plan view. In the example shown in FIG. 14A, with respect to the plan view (when viewed from, e.g., towards the detection site O shown in FIG. 6A), an outer circumference of the first reflecting part 92 is circular, where the diameter of the circle is, e.g., 200 μm to 11,000 μm. In the example shown in FIG. 14A, the wall part (92-2) of the first reflecting part 92 surrounds the light-emitting element 14 (see FIG. 6A). The outer circumference of the first reflecting part 92 may also be a quadrilateral (or specifically, a square) with respect to the plan view as shown, e.g., in FIG. 14B. Also, in the examples shown in FIGS. 14A and 14B, with respect to the plan view (when viewed from, e.g., towards the detection site O shown in FIG. 6A), the outer circumference of the light-emitting element 14 is a quadrilateral (or specifically, a square), where the length of one side of the square is, e.g., 100 μm to 10,000 μm. The outer circumference of the light-emitting element 14 may also be circular.

The first reflecting part 92 is made of metal whose surface is polished to a mirror finish, and thereby has a reflective structure (or specifically, a mirror reflection structure). The first reflecting part 92 may also be formed from, e.g., a resin whose surface is polished to a mirror finish. Specifically, for example, a base metal forming a base of the first reflecting part 92 is readied, and a surface of the base metal is then, e.g., subjected to plating. Alternatively, a mold of the first reflecting part 92 (not shown) is filled with a thermoplastic resin, molding is performed, and a metal film, for example, is then deposited by vapor deposition on a surface of the mold.

In the examples shown in FIGS. 14A and 14B, in plan view (when viewed from, e.g., towards the detection site O shown in FIG. 6A), a region of the first reflecting part 92 other than that directly supporting the light-emitting element 14 (i.e., the inner wall surface 92-2 and the top surface 92-3 of the wall part, and a part of the support part 92-1) is exposed. The exposed region is shown as a mirror surface part 92-4 in FIG. 13A. Although in the example shown in FIG. 13A, a dotted line representing the mirror surface part 92-4 is shown within the first reflecting part 92, the mirror surface part 92-4 is actually formed on a surface of the first reflecting part 92.

In the examples shown in FIGS. 13A, 13B, and 13C, the mirror surface part 92-4 preferably has a high reflectivity. The reflectivity of the mirror surface part 92-4 is, e.g., 80% to 90% or higher. It is possible for the mirror surface part 92-4 to be formed only on the inclined surface of the inner wall surface 92-2. In an instance in which the mirror surface part 92-4 is formed not only on the inclined surface of the inner wall surface 92-2 but also on the support part 92-1, the directivity of the light-emitting element 14 increases further.

The second reflecting part 18 is formed from, e.g., a resin whose surface (i.e., a reflecting surface on a side towards the light-receiving element 16 in FIG. 6A) is polished to a mirror finish, and thereby has a reflective structure (or specifically, a mirror reflection structure). In other words, the second reflecting part 18 is capable of causing mirror reflection of light without causing diffuse reflection of light. In an instance in which the second reflecting part 18 has a mirror reflection structure, the second reflecting part 18 is also capable of not causing reflected light R1" (i.e., directly reflected light; invalid light) produced by reflection of the first light R1 to reflect towards the light-receiving element 16, the reflected light R1" having a reflection angle that is different to that of the reflected light R1' produced by reflection of the first light R1 (see FIG. 6A). In such an instance, the detection accuracy of the biological information detector is further increased. As shown in FIG. 6A, since the reflected light R1' produced by reflection of the first light R1 originates from the detection site O, which is within the test subject, the reflection angle of the reflected light R1' produced by reflection of the first light R1 (i.e., a reflection angle relative to a straight line perpendicular to the surface SA of the test subject) is generally small. Meanwhile, since the reflected light R1" produced by reflection of the first light R1 originates from the surface SA of the test subject, the reflection angle of the reflected light R1" produced by reflection of the first light R1 is generally large.

Figure 16:
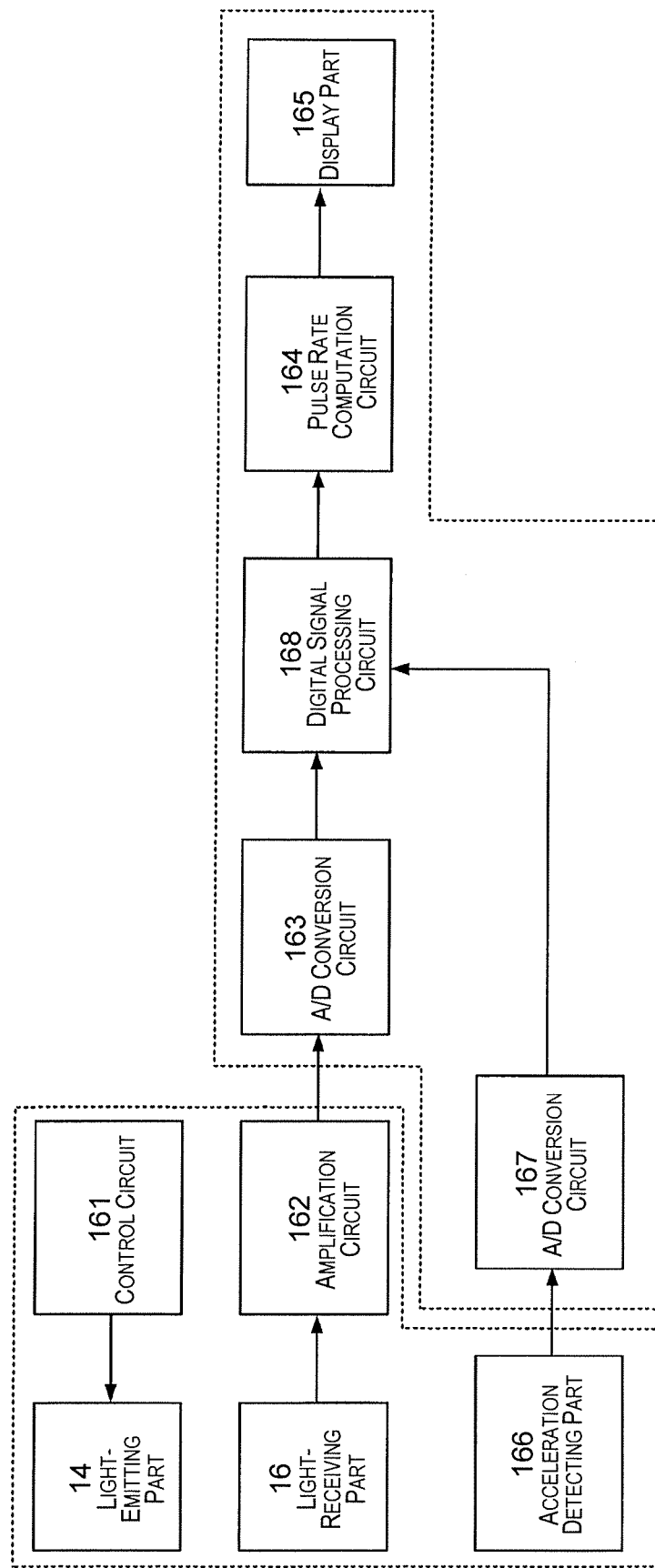
FIG. 16 is an example of a configuration of the biological information measuring device.

In FIG. 16 of Patent Citation 1, there is disclosed a reflecting part 131; and according to paragraphs [0046], [0059], and [0077] in Patent Citation 1, the reflecting part 131 has a diffuse reflection structure, and the reflectivity is increased to improve the efficiency of the light-receiving element 12. However, at the time of filing, it had not been recognized by those skilled in the art that in the reflecting part 131 according to Patent Citation 1, directly reflected light (or in a broader sense, noise) is also reflected towards the light-receiving element 12. In other words, the inventors recognized that reducing a noise component arising from the directly reflected light from a light reception signal increases the efficiency of the light-receiving element. Specifically, the inventors recognized that the detection accuracy of the biological information detector is further increased in an instance in which the second reflecting part 18 has a mirror reflection structure.

3. Biological Information Measuring Device
3.1 Pulse Rate Monitor

FIGS. 15A and 15B are examples of the outer appearance of a biological information measuring device comprising the biological information detector such as that shown in FIG. 1 and other drawings. As shown in FIG. 15A, the biological information detector shown, e.g., in FIG. 6A may further comprise a wristband 150 capable of attaching the biological information detector to an arm (or specifically, a wrist) of the test subject (i.e., the user). In the example shown in FIG. 15A, the biological information is the pulse rate indicated by, e.g., "72." The biological information detector is installed in a wristwatch showing the time (e.g., "8:15 am"). As shown in FIG. 15B, an opening part is provided to a back cover of the wristwatch, and the contact part 19 shown in, e.g., FIG. 6A is exposed in the opening part. In the example shown in FIG. 15B, the second reflecting part 18 and the light-receiving element 16 are installed in a wristwatch. In the example shown in FIG. 15B, the first reflecting part 92, the light-emitting element 14, the wristband 150, and other components are not shown.

FIG. 16 is an example of a configuration of the biological information measuring device. The biological information measuring device includes the biological information detector as shown, e.g., in FIG. 6A, and a biological information measuring part for measuring biological information from a light reception signal generated at the light-receiving element 16 of the biological information detector. As shown in FIG. 16, the biological information detector may have the light-emitting element 14, the light-receiving element 16, and a circuit 161 for controlling the light-emitting element 14. The biological information detector may further have a circuit 162 for amplifying the light reception signal from the light-receiving element 16. The biological information measuring part may have an A/D conversion circuit 163 for performing A/D conversion of the light reception signal from the light-receiving element 16, and a pulse rate computation circuit 164 for calculating the pulse rate. The biological information measuring part may further have a display part 165 for displaying the pulse rate.

The biological information detector may have an acceleration detecting part 166, and the biological information measuring part may further have an A/D conversion circuit 167 for performing A/D conversion of an acceleration signal from the acceleration detecting part 166 and a digital signal processing circuit 168 for processing a digital signal. The configuration of the biological information measuring device is not limited to the example shown in FIG. 16. The pulse rate computation circuit 164 in FIG. 16 may be, e.g., an MPU (i.e., a micro processing unit) of an electronic device installed with the biological information detector.

The control circuit 161 in FIG. 16 drives the light-emitting element 14. The control circuit 161 is, e.g., a constant current circuit, delivers a predetermined voltage (e.g., 6 V) to the light-emitting element 14 via a protective resistance, and maintains a current flowing to the light-emitting element 14 at a predetermined value (e.g., 2 mA). The control circuit 161 is capable of driving the light-emitting element 14 in an intermittent manner (e.g. at 128 Hz) in order to reduce consumption current. The control circuit 161 is formed on, e.g., a motherboard, and wiring between the control circuit 161 and the light-emitting element 14 is formed, e.g., on the substrate 11 shown in FIG. 6A.

The amplification circuit 162 shown in FIG. 16 is capable of removing a DC component from the light reception signal (i.e., an electrical current) generated in the light-receiving element 16, extracting only an AC component, amplifying the AC component, and generating an AC signal. The amplification circuit 162 removes the DC component at or below a predetermined wavelength using, e.g., a high-pass filter, and buffers the AC component using, e.g., an operational amplifier. The light reception signal contains a pulsating component and a body movement component. The amplification circuit 162 or the control circuit 161 is capable of feeding a power supply voltage for operating the light-receiving element 16 at, e.g., reverse bias to the light-receiving element 16. In an instance in which the light-emitting element 14 is intermittently driven, the power supply to the light-receiving element 16 is also intermittently fed, and the AC component is also intermittently amplified. The amplification circuit 162 is formed on, e.g., the mother board, and wiring between the amplification circuit 162 and the light-receiving element 16 is formed on, e.g., the substrate 11 shown in FIG. 6A. The amplification circuit 162 may also have an amplifier for amplifying the light reception signal at a stage prior to the high-pass filter. In an instance in which the amplification circuit 162 has an amplifier, the amplifier is formed, e.g., on the substrate 11.

The A/D conversion circuit 163 shown in FIG. 16 converts an AC signal generated in the amplification circuit 162 into a digital signal (i.e., a first digital signal). The acceleration detecting part 166 shown in FIG. 16 calculates, e.g., acceleration in three axes (i.e., x-axis, y-axis, and z-axis) and generates an acceleration signal. Movement of the body (i.e., the arm), and therefore movement of the biological information measuring device, are reflected in the acceleration signal. The A/D conversion circuit 167 shown in FIG. 16 converts the acceleration signal generated in the acceleration detecting part 166 into a digital signal (i.e., a second digital signal).

The digital signal processing circuit 168 shown in FIG. 16 uses the second digital signal to remove or reduce the body movement component in the first digital signal. The digital signal processing circuit 168 may be formed with, e.g., an FIR filter or another adaptive filter. The digital signal processing circuit 168 inputs the first digital signal and the second digital signal into the adaptive filter and generates a filter output signal in which noise has been removed or reduced.

The pulse rate computation circuit 164 shown in FIG. 16 uses e.g. fast Fourier transform (or in a broader sense, discrete Fourier transform) to perform a frequency analysis on the filter output signal. The pulse rate computation circuit 164 identifies a frequency that represents a pulsating component based on a result of the frequency analysis, and calculates a pulse rate.

3.2 Pulse Oximeter

A description will now be given for a pulse oximeter as another example of the biological information measuring device. A biological information detector (or in a broader sense, an optical device) that is installed in the pulse oximeter can be obtained using a configuration that is identical to that used in the above-described embodiment (i.e., the configuration shown in, e.g., FIG. 6A or FIG. 1A).

A description will now be given based on the configuration shown in FIG. 6A. The pulse oximeter (or in a broader sense, the biological information detector) comprises the light-emitting element 14 and the light-receiving element 16. The light-emitting element 14 emits, e.g., a red light and infrared light. Reflected light, produced by the light emitted by the light-emitting element 14 reflecting at the detection site O (e.g., a blood vessel), is measured using the light-receiving element 16. Red-light and infrared absorbance of haemoglobin in the blood differ depending on presence of a bond with oxygen. Therefore, the arterial oxygen saturation ($S_pO_2$) can be measured by measuring the reflected light at the light-receiving element 16 and analyzing the reflected light.

The configuration of the biological information measuring part (i.e., the A/D conversion circuit 163, the pulse rate computation circuit 164, the display part 165, the acceleration detecting part 166, the A/D conversion circuit 167, and the digital signal processing circuit 168) for use in a pulse rate monitor as shown in FIG. 16 can be used as a configuration of the biological information measuring part for use in the pulse oximeter. However, the pulse rate computation circuit 164 shown in FIG. 16 is replaced by an arterial oxygen saturation analysis circuit 164 in which a pulse rate computation circuit and an FFT or another approach is used.

Although a detailed description was made concerning the present embodiment as stated above, persons skilled in the art should be able to easily understand that various modifications can be made without substantially departing from the scope and effects of the invention. Accordingly, all of such examples of modifications are to be included in the scope of the invention. For example, terms stated at least once together with different terms having broader sense or identical sense in the specification or drawings may be replaced with those different terms in any and all locations of the specification or drawings.

The entire disclosure of Japanese Patent Application No. 2010-33058, filed Feb. 18, 2010 is expressly incorporated by reference herein.

What is claimed is:

1. An optical device, comprising:
   a substrate having a first surface and a second surface that is opposite the first surface;
   a light-emitting element having a first center;
   a light-receiving element having a second center, the light-receiving element being installed at a side of the first surface, the light-receiving element further having a rectangular shape with respect to a plan view as viewed in a normal direction relative to the first surface or the second surface, at least a part of the light-emitting element being arranged at a position that overlaps the light-receiving element with respect to the plan view;
   a bonding pad being provided at a position that is displaced relative to the second center towards a first direction which is perpendicular to the normal direction, the bonding pad being disposed adjacent to a corner of the light-receiving element with respect to the plan view;

a first reflecting part configured to reflect light emitted by the light-emitting element, the first reflecting part including a first side part and a second side part opposite the first side part, the first side part being disposed on the second surface of the substrate, the light-emitting element being disposed on the second side part, the first reflecting part having a center axis that extends in the normal direction through a diameter center of a diameter of the first reflecting part in the first direction, the first center being provided at a position that is displaced relative to the second center towards a second direction, which is opposite the first direction and in a direction away from the first center, with respect to the plan view, the first center of the light-emitting element aligning the center axis of the first reflecting part with respect to the plan view.

2. The optical device according to claim 1, wherein
the light-emitting element has a rectangular profile with respect to the plan view; wherein
one side of the rectangle profile of the light-emitting element is tangent to a circle having a given radius and having a fourth center positioned on the bonding pad with respect to the plan view.

3. The optical device according to claim 1, wherein
the light-emitting element has a rectangular profile with respect to the plan view; wherein
one side of the rectangle profile of the light-emitting element is perpendicular to a direction in which the first center and the second center are connected, with respect to the plan view.

4. The optical device according to claim 1, wherein
the entirety of the light-emitting element is arranged at a position at which there is a complete overlapping of the light-receiving element with respect to the plan view.

5. A biological information detector, comprising:
optical device according to of claim 1,
a contact part formed from a material that is transparent with respect to a wavelength of light emitted by the light-emitting element, the contact part having a surface in contact with a test subject; and
a second reflecting part configured to reflect light having biological information; wherein
the light-emitting element emits light directed at a detection site of the test subject;
the light-receiving element receives light having biological information, the light being light emitted by the light-emitting element and reflected at the detection site;
the substrate is a flexible substrate formed from a material that is transparent with respect to the wavelength of light emitted by the light-emitting element; and
the biological information is a pulse rate.

\* \* \* \* \*